(12) United States Patent
Kimura et al.

(10) Patent No.: US 8,974,417 B2
(45) Date of Patent: Mar. 10, 2015

(54) INSTRUMENT FOR AN ENDOSCOPE AND NEEDLE FOR AN ENDOSCOPE

(75) Inventors: Koh Kimura, Sagamihara (JP); Kiyotaka Matsuno, Sagamihara (JP); Ken Fujisaki, Tokyo (JP)

(73) Assignee: Olympus Corporation, Tokyo (JP)

( * ) Notice: Subject to any disclaimer, the term of this patent is extended or adjusted under 35 U.S.C. 154(b) by 1999 days.

(21) Appl. No.: 11/440,616

(22) Filed: May 25, 2006

(65) Prior Publication Data

US 2006/0282048 A1 Dec. 14, 2006

Related U.S. Application Data

(63) Continuation of application No. PCT/JP2004/017693, filed on Nov. 29, 2004.

(30) Foreign Application Priority Data

Nov. 28, 2003 (JP) ................ P2003-398834
Feb. 19, 2004 (JP) ................ P2004-043215

(51) Int. Cl.
*A61M 5/178* (2006.01)
*A61B 17/34* (2006.01)
*A61M 25/00* (2006.01)

(52) U.S. Cl.
CPC ......... *A61B 17/3478* (2013.01); *A61B 17/3496* (2013.01); *A61M 25/0084* (2013.01)
USPC ........................................... 604/158; 604/21

(58) Field of Classification Search
USPC ................ 600/156, 106; 604/158, 21
See application file for complete search history.

(56) References Cited

U.S. PATENT DOCUMENTS

| | | | |
|---|---|---|---|
| 4,791,937 A | 12/1988 | Wang | |
| 4,968,302 A | 11/1990 | Schluter et al. | |
| 6,193,717 B1 * | 2/2001 | Ouchi | 606/49 |

FOREIGN PATENT DOCUMENTS

| | | |
|---|---|---|
| DE | 40 25 503 A1 | 5/1991 |
| EP | 0 818 208 A2 | 1/1998 |
| JP | 64-500492 | 2/1989 |
| JP | 5-91686 | 12/1993 |
| JP | 10-277150 | 10/1998 |

(Continued)

OTHER PUBLICATIONS

English-language Abstract only of JP 10-277150.
Full English-language Translation only of JP 5-091686.

*Primary Examiner* — Kevin C. Sirmons
*Assistant Examiner* — Deanna K Hall
(74) *Attorney, Agent, or Firm* — Scully, Scott, Murphy & Presser, P.C.

(57) ABSTRACT

A needle for an endoscope, includes: an outer sheath tube having a fluid passage provided therein; a distal end discharging portion that is accommodated in the distal end of the outer sheath tube so as to be extended therefrom and retracted thereinto, and is connected to the distal end of the fluid passage; an operating device for operating the distal end discharging portion so as to be extended from the distal end of the outer sheath tube and retracted thereinto; a fluid supplying device, that is provided in the outer sheath tube and is caused to communicate with the fluid passage, and supplies a fluid to the distal end discharging portion through the fluid passage; and a blocking device that is provided in the fluid passage, for freely opening and shutting off circulation of a fluid in line with an operation of the operating device.

4 Claims, 13 Drawing Sheets

(56) References Cited

FOREIGN PATENT DOCUMENTS

| JP | 2001-058006 | 3/2001 | | |
| JP | 2001058006 A | * 3/2001 | ............. | A61M 5/14 |
| WO | WO 88/00066 | 1/1988 | | |
| WO | WO 00/09185 | 2/2000 | | |
| WO | WO 00/33908 | 6/2000 | | |
| WO | WO 2004/020032 A1 | 3/2004 | | |

* cited by examiner

INSTRUMENT FOR AN ENDOSCOPE AND NEEDLE FOR AN ENDOSCOPE

PRIORITY CLAIM

This application is continuation application of a PCT Application No. PCT/JP2004/017693, filed on Nov. 29, 2004, entitled "INSTRUMENT FOR AN ENDOSCOPE AND NEEDLE FOR AN ENDOSCOPE" whose priority is claimed on Japanese Patent Application No. 2004-43215 filed on Feb. 19, 2004, and Japanese Patent Application No. 2003-398834 filed on Nov. 28, 2003. The description thereof is incorporated herein by reference.

BACKGROUND OF THE INVENTION

1. Field of the Invention

The present invention relates to an instrument for an endoscope, which is inserted into a body cavity through a channel of the endoscope and injects a drug solution into a tissue region in the body cavity, that is, a needle for an endoscope.

2. Description of the Related Art

As one of the techniques carried out by an endoscope, there is a technique by which an injection needle is inserted into a body cavity through the channel of the endoscope and which injects a drug solution, etc., into a lesion in the body cavity. As a treatment instrument used for the technique, a needle for an endoscope, which has a double-tube structure, has been proposed. The needle for an endoscope is provided with an inner tube to which a hollow needle is connected, and an outer tube for retaining the inner tube, which is inserted in the interior thereof, so as to extend and retract the same, for example, as disclosed in Japanese Published Unexamined Patent Application No. 2001-58006.

The way of using the needle for an endoscope is as follows. First, both tubes are inserted into the channel and are inserted into a body cavity. Next, a needle is extended from the distal end of the outer tube by pushing the inner tube into the outer tube, and is inserted into a bodily tissue in the body cavity, wherein a drug solution supplied in the inner tube is injected.

Also, in a field differing from injection, a derivation biopsy needle has been proposed as a treatment instrument for inserting a needle into a body cavity as disclosed in, for example, U.S. Pat. No. 4,791,937, which suctions bodily tissue by inserting a hollow needle for biopsy.

Japanese Published Patent Application No. 2001-58006 discloses a needle for an endoscope, which endoscopically injects various types of drug solutions into a tissue or blood vessel via an inner tube. With respect to a method for use, a syringe is attached to the ferrule at the proximal end of the inner tube, and a drug solution to be used is filled in the inner tube. Also, a needle for an endoscope is inserted into the channel of the endoscope, and the distal end of the tube is extended from the distal end of the endoscope. After that, the inner tube is extended from the outer tube, and a needle tip secured at the distal end of the inner tube is inserted into a tissue or blood vessel, whereby the drug solution can be injected into the tissue or blood vessel by pushing the syringe.

SUMMARY OF THE INVENTION

The invention provides an instrument for an endoscope, including: an outer sheath tube internally provided with a fluid passage; a distal end injection portion accommodated in the distal end of the outer sheath tube so as to be extended and retracted, and connected to the distal end of the fluid passage; operating device provided at the proximal portion of the outer sheath tube for operating the distal end injection portion so as to be extended and retracted from the distal end of the outer sheath tube; fluid circulating means provided in the outer sheath tube, communicating with the fluid passage, and circulating a fluid to the distal end injection portion via the fluid circulating portion; and blocking device provided in the fluid passage for opening and closing circulation of a fluid in line with operations of the operating device.

In the instrument for an endoscope according to the invention, it is preferable that the distal end injection portion is a hollow needle and the outer sheath tube for accommodating the hollow needle is insertable into the channel of the endoscope.

In the instrument for an endoscope according to the invention, it is preferable that the blocking device blocks circulation of a fluid in the fluid passage only in a state where the hollow needle is accommodated in the outer sheath tube by operating the operating device.

In the instrument for an endoscope according to the invention, it is preferable that the operating device is provided with a wire connected to the hollow needle, and the blocking device is provided with a sealing member secured at an intermediate part of the wire and made of a resilient material, and an orifice for opening and closing the fluid passage by the sealing member is inserted into and retracted from in line with movement of the wire to the hollow needle.

The invention provides an instrument for an endoscope including: an outer sheath tube; a hollow needle accommodated in the outer sheath tube and having a side hole; a wire connected to the hollow needle for driving the hollow needle so as to be extended from and retracted into the distal end of the outer sheath tube; a ferrule member attached to the proximal end of the outer sheath tube, which is able to circulate a fluid from the distal end of the hollow needle through the outer sheath tube and via the side hole of the hollow needle; distal end fluid-tight keeping means provided at the distal end side from the side hole of the hollow needle, which keeps fluid-tight the outer circumferential surface of the hollow needle and the inner wall of the outer sheath tube; and proximal end fluid-tight keeping means for keeping fluid-tight the inner wall of the ferrule member and the wire; and further including: a sealing member provided at an intermediate portion of the wire; and an orifice for blocking circulation of a fluid so as to be opened and closed between the ferrule member and the hollow needle by inserting and removing the sealing member in line with extension and retraction of the hollow needle from and into the distal end of the outer sheath tube.

The invention provides a needle for an endoscope, including: an outer sheath tube having a fluid passage internally formed; a hollow needle accommodated so as to be extended and retracted from the distal end of the outer sheath tube for excreting a fluid supplied through the fluid passage; and an operating device operated at the proximal end of the outer sheath tube for protruding the hollow needle from the distal end of the outer sheath tube and retracting the same thereinto, wherein a diameter-reduced portion is formed at the distal end of the outer sheath tube, and a diameter-enlarged portion, which is brought into contact with the diameter-reduced portion when protruding the hollow needle from the distal end of the outer sheath tube and blocks the distal end of the outer sheath tube, is formed at the hollow needle.

In the needle for an endoscope according to the invention, it is preferable that a sealing member which is brought into contact with the diameter-reduced portion and is made coherent thereto be provided in the hollow needle.

In the needle for an endoscope according to the invention, it is preferable that the sealing member be provided at the front end of the diameter-enlarged portion. Further, it is preferable that the sealing member be brought into contact with the diameter-reduced portion and is made coherent to the diameter-reduced portion by resilient deformation. Still further, it is also preferable that the sealing member be brought into contact with the diameter-reduced portion by protruding the hollow needle from the distal end of the outer sheath tube and be subjected to resilient deformation.

In the needle for an endoscope according to the invention, it is preferable that the sealing member be provided at the side face of the diameter-enlarged portion or at the rear end of the diameter-enlarged portion.

It is preferable that the sealing member be slidably brought into contact with the inside face of the outer sheath tube and is provided with fluid-tightness for preventing leakage of the drug solution to the inside face of the outer sheath tube. In addition, it is preferable that the sealing member be made coherent to the inside face of the outer sheath tube by resilient deformation. Further, it is preferable that the sealing member be disposed inside the outer sheath tube by being pushed into the interior of the outer sheath tube and be subjected to resilient deformation.

In the needle for an endoscope according to the invention, it is preferable that at least any one of the diameter-enlarged portion and the diameter-reduced portion be made of a resilient body. It is preferable that, by resilient deformation of either one of them, both be made coherent to each other.

In the needle for an endoscope according to the invention, it is preferable that the diameter of the outer circumferential surface of the diameter-enlarged portion be gradually enlarged from the distal end of the outer sheath tube to the proximal end thereof, the diameter of the inner circumferential surface of the diameter-reduced portion be gradually enlarged from the distal end of the outer sheath tube to the proximal end thereof, and the inner circumferential surface of the diameter-reduced portion be brought into contact with the outer circumferential surface of the diameter-enlarged portion.

In the needle for an endoscope according to the invention, it is preferable that the length of the diameter-reduced portion along the moving direction of the hollow needle be longer than the moving distance of the hollow needle when it is retracted from the distal end of the outer sheath tube, and, even in a state where the hollow needle is retracted from the distal end of the outer sheath tube, the distal end of the hollow needle be disposed inside the diameter-reduced portion.

In the needle for an endoscope according to the invention, it is preferable that the operating device be provided with a wire one end of which is connected to the hollow needle and the other end of which is operated at the proximal end side of the outer sheath tube, and the operating device permits the hollow needle to be extended from and retracted into the distal end of the outer sheath tube by extending and retracting the other end of the wire, which is inserted into the outer sheath tube, in the interior of the outer sheath tube.

In the needle for an endoscope according to the invention, it is preferable that the hollow needle be disposed so that the center axis of the hollow needle diagonally crosses the center axis of the diameter-reduced portion by bending the wire.

The invention provides a needle for an endoscope including: a hollow needle, accommodated so as to extend from and retract into the distal end of the outer sheath tube, for discharging a fluid supplied through the fluid passage; and an operating device, operated at the proximal end of the outer sheath tube, for causing the hollow needle to extend from and retract into the distal end of the outer sheath tube; wherein a cover portion to block the distal end of the outer sheath tube is formed, and the cover portion is formed of an elastic material through which the hollow needle can pass.

The invention provides a needle for an endoscope, including: an outer sheath tube having a fluid passage internally formed therein; a hollow needle, accommodated so as to be extended from and retracted into the distal end of the outer sheath tube, for discharging a fluid supplied through the fluid passage; and an operating device, operated at the proximal end of the outer sheath tube, for extending the hollow needle from and retracting the same into the distal end of the outer sheath tube; wherein the operating device is provided with a wire inserted into the outer sheath tube, one end of the wire is connected to the hollow needle and the other end thereof is operated at the proximal end side of the outer sheath tube, the length of the wire is set to a length at which the hollow needle is held up and is retained at a fixed position in a state where the hollow needle is extended from the distal end of the outer sheath tube, and the operating device causes the hollow needle to be extended from and retracted into the distal end of the outer sheath tube by extending and retracting the other end of the wire into the interior of the outer sheath tube.

In the needle for an endoscope according to the invention, it is preferable that both the hollow needle and the wire are made of metallic materials, and one end of the wire is welded to the proximal end of the hollow needle.

In the needle for an endoscope according to the invention, it is preferable that a hole portion penetrating through the tubular wall be formed at the proximal end side of the hollow needle.

BRIEF DESCRIPTION OF THE DRAWINGS

FIG. 2 is a side view depicting a needle for an endoscope according to Embodiment 1 of the invention, which depicts a state where a slide section is pushed in.

DETAILED DESCRIPTION OF THE INVENTION

A description is given of Embodiment 1 of a needle for an endoscope according to the invention with reference to FIG. 1 through FIG. 6.

Figure 1:
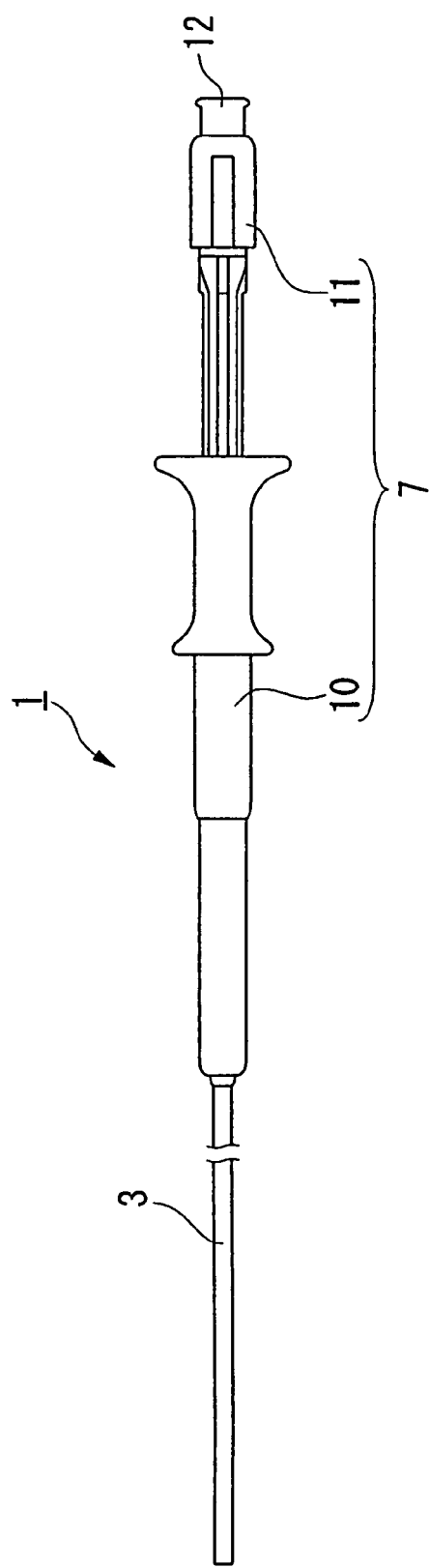
FIG. 1 is a side view depicting a needle for an endoscope according to Embodiment 1 of the invention, which depicts a state where a slide section is retracted.
Figure 2:
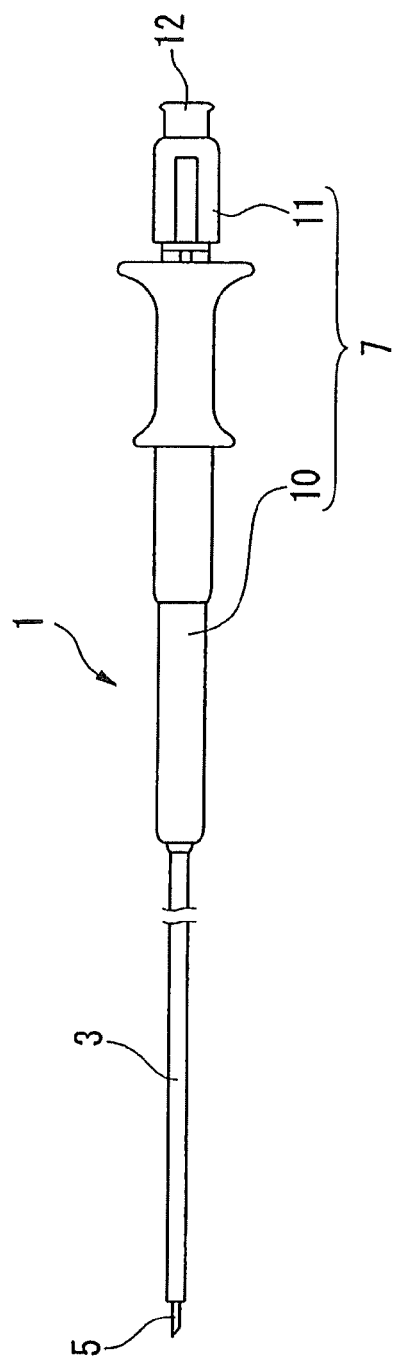
Figure 3:
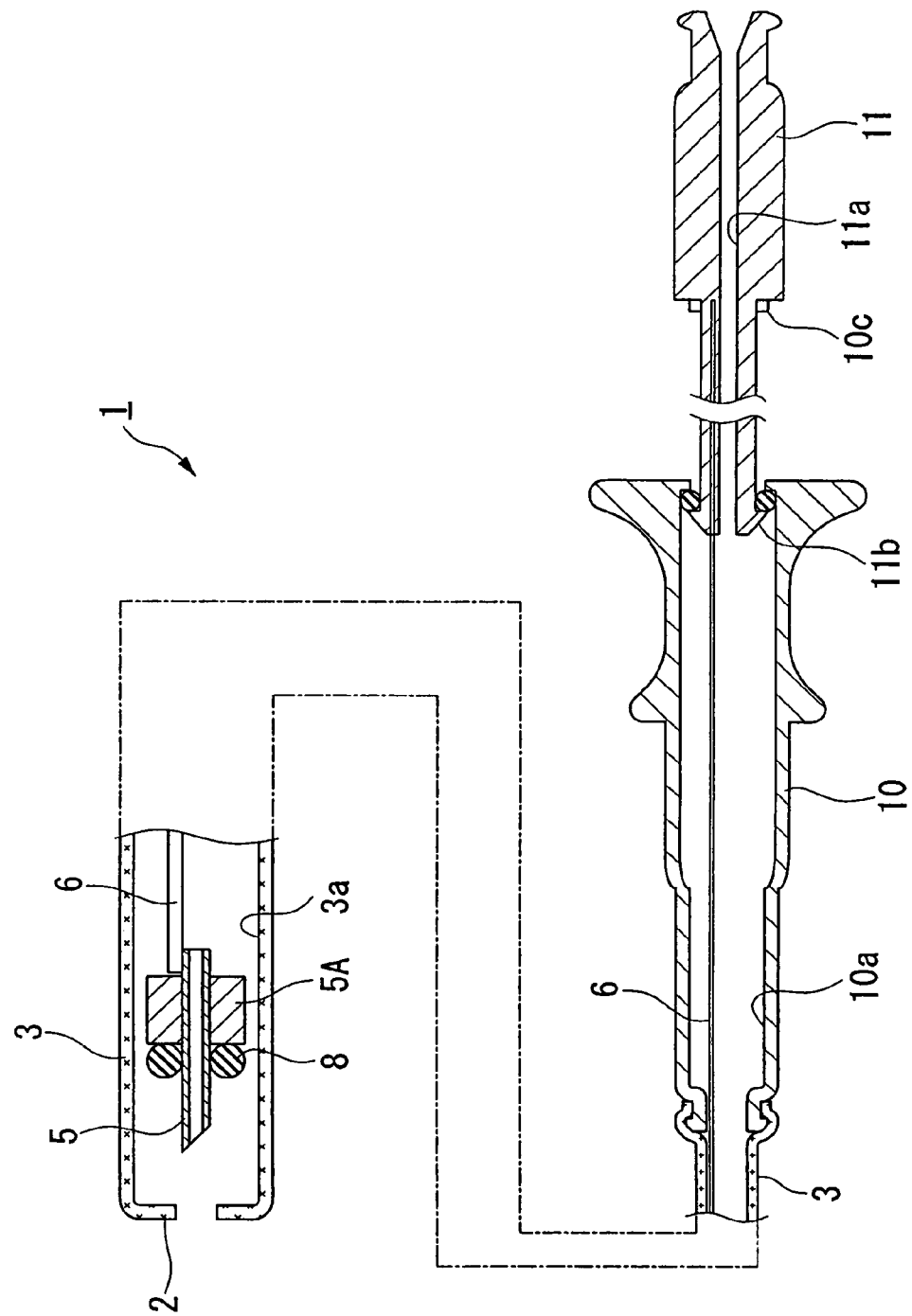
FIG. 3 is a sectional view depicting a needle for an endoscope according to Embodiment 1 of the invention along its axial direction.

As depicted in FIG. 1 through FIG. 3, a needle 1 for an endoscope according to the present embodiment includes an outer sheath tube 3, a hollow needle 5, and an operation portion (operating device) 7. The outer sheath tube 3 is made of a resin material such as fluorine, polyamide, polyethylene, etc., which presents a cylindrical shape whose section is circular. A fluid passage 3a is formed in the interior of the outer sheath tube 3. The hollow needle 5 is accommodated in the interior of the outer sheath tube 3 so as to be extended from and retracted into the distal end of the outer sheath tube 3, which discharges a fluid, supplied through the fluid passage 3a, through a needle tip. The operation portion 7 is operated at the proximal end of the outer sheath tube 3 and causes the hollow needle 5 to be extended from and retracted into the distal end of the outer sheath tube 3.

A diameter-reduced portion 2 is formed at the distal end of the outer sheath portion 3 so as to form a partitioning wall on the outer end face. A small circular hole is formed at the center of the diameter-reduced portion 2. The hollow needle 5 extends its needle tip through the small hole. A diameter-enlarged portion 5A which is enlarged in the diametrical direction with the needle body disposed in the center is provided at the hollow needle 5. The diameter-enlarged portion 5A is provided integrally with or separately from the hollow needle 5, wherein a slight clearance is secured between the outer circumferential surface of the diameter-enlarged portion 5A and the inside face of the outer sheath tube 3.

Where it is assumed that the direction oriented from the proximal end of the outer sheath tube 3 to the distal end thereof is forward (or front) and the direction oriented from the distal end of the outer sheath tube 3 to the proximal end thereof is backward (or back), an O-ring (sealing member) 8 is provided at the forward end of the diameter-enlarged portion 5A, which is brought into contact with the diameter-reduced portion 2 and made coherent thereto when the hollow needle 5 moves in the forward direction. The O-ring 8 is made of a resiliently deformable resin material. The outer diameter of the O-ring 8 is smaller than the inner diameter of the outer sheath tube 3 and is set to a size which is not brought into contact with the inside face of the outer sheath tube 3. In addition, the inner diameter of the O-ring 8 is smaller than the outer diameter of the hollow needle 5, wherein the O-ring 8 has the hollow needle 5 pushed inside of the O-ring 8 and is made coherent to the outer circumferential surface with its own elastic force so as not to be easily come apart from the hollow needle 5. When the O-ring 8 is pushed into the diameter-reduced portion 2, it is resiliently deformed and is made coherent to the inside face of the diameter-reduced portion 2. In this state, the O-ring 8 can exert high fluid-tightness so that no drug solution leaks out of the diameter reduced portion 2, except the needle hole of the hollow needle 5.

Further, in order to prevent the O-ring 8 from being separated from the hollow needle 5, it is further preferable that the inner circumferential surface of the O-ring 8 is formed to be flat, or minute projections and/or dents are formed on the inner circumferential surface of the O-ring 8 and on the outer circumferential surface of the hollow needle 5, thereby increasing mutual friction resistance. Still further, the O-ring 8 may have various sectional shapes including not only a circular shape, but also an oval shape, an elliptical shape, and a square shape.

The operation portion 7 includes a wire 6 inserted into the outer sheath tube 3, an operation portion body 10 for operating the wire 6 at the proximal end side of the outer sheath tube 3 and a sliding portion 11. The wire 6 has one end connected to the rear end of the hollow needle 5, and the other end connected to the sliding portion 11. A single stainless steel wire whose diameter is, for example, 0.3 through 0.5 mm is used as the wire 6, and the wire 6 is connected to the outer circumferential surface at the proximal end side of a metal hollow needle 5 by brazing or welding.

In the operation portion 7, the wire 6 is extended and retracted into the interior of the outer sheath tube 3 by pushing the sliding portion 11 into the operation portion body 10 and pulling out the same therefrom, whereby the distal end of the hollow needle 5 is extended from and retracted into the distal end of the outer sheath tube 3.

A through-hole 10a communicating with the fluid passage 3a in the interior of the outer sheath tube 3 is formed in the operation portion body 10. A piston portion 11b slidably brought into contact with the through-hole 10a is provided in the sliding portion 11. Also, a through-hole 11a communicating with the fluid passage 3a in the interior of the outer sheath tube 3 via the through-hole 10a is formed in the sliding portion 11. The through-hole 11a is opened to the proximal end of the sliding portion 11, and a ferrule 12 is secured at the opening portion, wherein it is possible to supply a drug solution from the ferrule 12 into the interior of the outer sheath tube 3 through the through-holes 11a and 10a. Further, an annular member 10c is provided in the sliding portion 11, which is fitted into the through-hole 10a when the sliding portion 11 is pushed into the operation portion body 10 and fixes the sliding portion 11 at the operation portion body 10.

Next, a description is given of a method for use, actions and effects of the needle 1 for an endoscope according to the embodiment.

First, the outer sheath tube 3 is inserted into the channel of an endoscope with the distal end of the hollow needle 5 accommodated in the outer sheath tube 3, thereby causing the distal end of the outer sheath tube 3 from the distal end of the endoscope to be extended. Also, a drug solution is filled in advance in the fluid passage 3a of the outer sheath tube 3.

After the distal end of the outer sheath tube 3 is extended from the distal end of the endoscope, the sliding portion 11 is pushed into the operation portion body 10 to cause the wire 6 to be extended in the interior of the outer sheath tube 3. If the wire 6 is extended, the hollow needle 5 connected to the distal end of the wire 6 is also advanced in the interior of the outer sheath tube 3.

Figure 4:
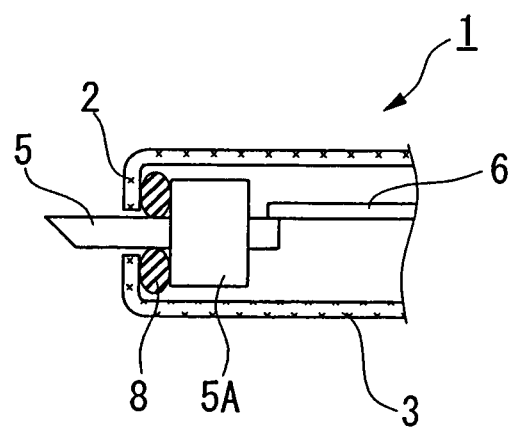
FIG. 4 is a sectional view depicting the major parts of a needle for an endoscope according to Embodiment 1 of the invention along its axial direction.

By further pushing the sliding portion 11 into the operation portion body 10, the wire 6 is advanced in the interior of the outer sheath tube 3, wherein if the sliding portion 11 is further pushed in even if the O-ring 8 is brought into contact with the diameter-reduced portion 2, the hollow needle 5 is extended from the distal end of the outer sheath tube 3 as depicted in FIG. 4, and at the same time, the O-ring 8 is pushed to the diameter-reduced portion 2 and is resiliently deformed, and then is made coherent to the inside face of the diameter-reduced portion 2. When the O-ring 8 is made coherent to the inside face of the diameter-reduced portion 2, the O-ring 8 exerts high fluid-tightness so that no drug solution leaks out from the diameter-reduced portion 2 except the needle hole of the hollow needle 5. As the sliding portion 11 is pushed until the O-ring 8 is made coherent to the diameter-reduced portion 2, the annular member 10c is fitted into the through-hole 10a, and the sliding portion 11 is fixed at the operation portion body 10. Since the sliding portion 11 is fixed at the operation portion body 10, the hollow needle 5 is fixed in a state where it is extended from the distal end of the outer sheath tube 3.

After the hollow needle 5 is extended from the distal end of the outer sheath tube 3, the outer sheath tube 3 inserted into the channel is operated so as to be extended from the distal end of the endoscope, wherein the needle tip of the hollow needle 5 is inserted into a bodily tissue. Also, a pressurizing device such as a syringe, etc., is mounted at the ferrule 12, and a drug solution filled in the fluid passage 3a is pressurized, wherein the drug solution is injected into the bodily tissue through the hollow needle 5.

According to the needle 1 for an endoscope, since the diameter-reduced portion 2 is blocked by the O-ring 8 when the hollow needle 5 is extended from the distal end of the outer sheath tube 3, there is no case where a drug solution leaks out of the outer sheath tube 3 through the diameter-reduced portion 2 even if injection pressure is given to the drug solution in the outer sheath tube 3.

Figure 5:
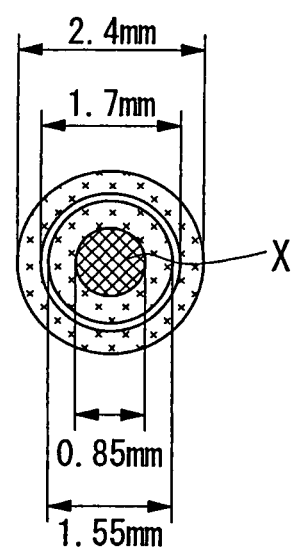
FIG. 5 is a sectional view of a conventional needle for an endoscope in the direction perpendicular to the axial direction thereof.
Figure 6:
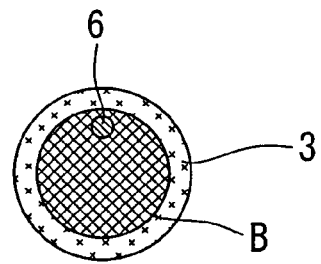
FIG. 6 is a sectional view of a needle for an endoscope according to Embodiment 1 of the invention in the direction perpendicular to the axial direction thereof.

The needle 1 for an endoscope is not composed of a double-tube structure as in the prior arts but is composed of a single-tube structure. Since there is no need to take the outer tube into consideration, it is possible to make the inner diameter of the outer sheath tube 3, through which a drug solution is supplied, larger than the inner diameter of the conventional inner tube. For example, in a case where, in a conventional double-tube structure type needle, the inner diameter and outer diameter of the outer tube are made in 1.7 mm and 2.4 mm, respectively, and the inner diameter and outer diameter of the inner tube are made in 0.85 mm and 1.55 mm, respectively, as depicted in FIG. 5, a drug solution can be supplied only in the portion having a section X of a tubular duct of the inner tube. However, in the needle 1 for an endoscope, in a case where the inner diameter and outer diameter of the outer sheath tube 3 are made the same as those of the outer tube, as depicted in FIG. 6, a drug solution can be supplied in a portion having a section B of the fluid passage 3a of the outer sheath tube 3. Therefore, the sectional area of the fluid passage can be increased by approximately 385% on the basis of calculation. Accordingly, the tubular resistance of the fluid passage 3a which is 1.5 through 2.5 m long can be remarkably reduced, and it is possible to smoothly operate the sliding portion 11 even where a drug solution having high viscosity is injected.

Also, according to the needle 1 for an endoscope, it is possible to reduce the outer diameter of the outer sheath tube 3 by making the sectional area of the fluid passage 3a identical to that of the conventional double-tube structure type needle, wherein it is possible to reduce the friction resistance between the channel and the outer sheath tube 3 by securing a large clearance between the channel of the endoscope and the outside face of the outer sheath tube 3, thereby securing smoother insertion of the outer sheath tube 3 into the channel. Further, when inserting the hollow needle 5 into a bodily tissue by further pushing the outer sheath tube 3, which is pushed into the channel, into the outer sheath tube 3, a sufficient force is applied to the hollow needle 5 to insert into the bodily tissue without applying an intensive force thereto. Therefore, it is possible to insert the hollow needle 5 into the bodily tissue with a slight force.

Also, even if the thickness of the outer sheath tube 3 is thickened with the sectional area of the fluid passage 3a made identical to that of the inner tube of the conventional double-tube structure needle, it is possible to make the outer diameter of the outer sheath tube 3 smaller than the outer diameter of the outer tube of the conventional double-tube structure injection needle, wherein it is possible to prevent the outer sheath tube 3 from being buckled when inserting the endoscope into the channel and when inserting the hollow needle 5 into a bodily tissue.

According to the needle 1 for an endoscope, since the hollow needle 5 and the wire 6 are connected to each other in a very general and inexpensive manner such as brazing and welding, the production costs can be further reduced in comparison with the prior arts.

In addition, since the wire 6 is connected to the outer circumferential surface at the proximal end side of the hollow needle 5, and the tubular duct of the hollow needle 5 can be kept linear, it is possible to feed a drug solution having high viscosity without applying an intensive force.

Further, since only the metal hollow needle 5 is made of a hard material among the components disposed at the distal end side of the outer sheath tube 3, if the length of the hollow needle 5 is made as short as possible, insertion of the outer sheath tube 3 into the endoscope and extension of the hollow needle 5 can be carried out only with a slight force even in a case where the distal end of the endoscope is bent to 240 degrees at maximum, for example, where the needle 1 for an endoscope is used especially for alimentary canals.

According to the needle 1 for an endoscope, since the O-ring 8 is constructed so that the outer diameter thereof is made smaller than the inner diameter of the outer sheath tube 3, and it is not brought into contact with the inside face of the outer sheath tube 3, the sliding resistance is remarkably small when extending and retracting the hollow needle 5 into the interior of the outer sheath tube 3, wherein excellent operation efficiency can be secured. However, in the embodiment, it is desired that the outer diameter of the O-ring 8 and the inner diameter of the outer sheath tube 3 be strictly controlled to such a degree that no drug solution leaks out of the clearance between the O-ring 8 and the inside face of the outer sheath tube 3 even if injection pressure is applied to the drug solution in the outer sheath tube 3. If a drug solution leaks out of the clearance between the O-ring 8 and the inside face of the outer sheath tube 3, the drug solution is needlessly consumed.

Figure 7:
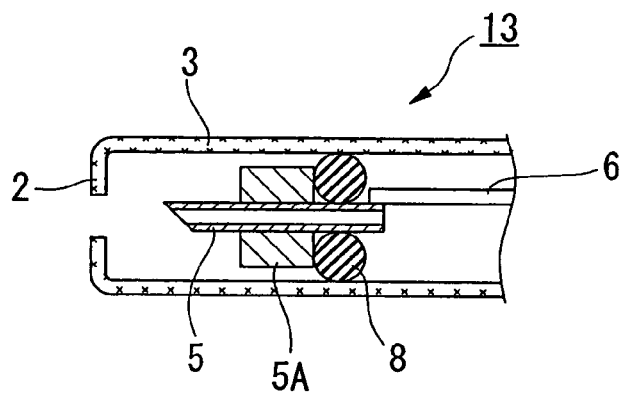
FIG. 7 is a sectional view depicting the major parts of a needle for an endoscope according to Embodiment 2 of the invention along the axial direction thereof.

Next, a description is given of Embodiment 2 of the needle for an endoscope according to the invention with reference to FIG. 7. Also, components which are similar to those of Embodiment 1 described above are given the same reference numerals, and description thereof is omitted.

In a needle 13 for an endoscope according to Embodiment 2, the O-ring 8 is disposed at the proximal end side of the diameter-enlarged portion 5A. As in Embodiment 1, the hollow needle 5 is pushed into the inside of the O-ring 8 so that it is not easily separated from the hollow needle 5, and the O-ring 8 is made coherent to the outer circumferential surface of the hollow needle 5 with its own elastic force.

The needle 13 for an endoscope may be used in the same manner as the needle 1 for an endoscope according to Embodiment 1, wherein similar actions and effects can be brought about. Furthermore, it is possible to suppress a turbulent flow region generated at the proximal end side of the diameter-enlarged portion 5A when a drug solution flows into the interior of the hollow needle 5. Also, it is possible to prevent air from flowing into the clearance between the diameter-enlarged portion 5A and the outer sheath tube 3.

Figure 8:
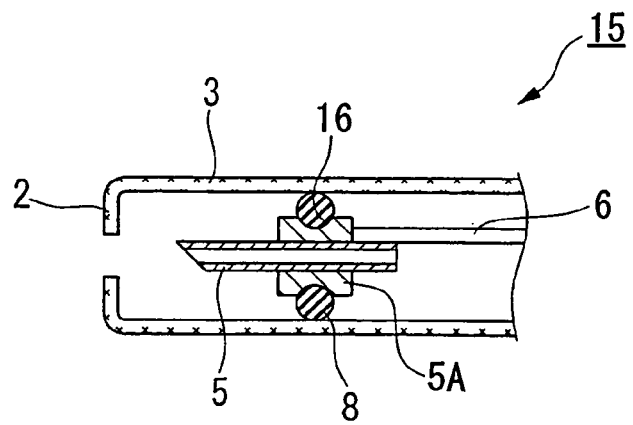
FIG. 8 is a sectional view depicting the major parts of a needle for an endoscope according to Embodiment 3 of the invention along the axial direction thereof.

Next, a description is given of Embodiment 3 of the needle for an endoscope according to the invention with reference to FIG. 8. Also, components which are similar to those of the respective embodiments described above are given the same reference numerals, and description thereof is omitted.

In the needle 15 for an endoscope according to the present embodiment, the O-ring 8 is disposed at the side of the diameter-enlarged portion 5A. Also, a groove 16 in which the O-ring 8 is fitted is provided at the side of the diameter-enlarged portion 5A in order to prevent the O-ring from dropping off. The O-ring 8 is pushed inside the diameter-enlarged portion 5A and is fitted in the groove 16 so that it does not easily drop from the diameter-enlarged portion 5A, and the O-ring 8 is made coherent to the diameter-enlarged portion 5A with its own elastic force.

The needle 15 for an endoscope may be used in the same manner as the needle 1 for an endoscope according to Embodiment 1, wherein the needle 15 brings about similar actions and effects. Furthermore, it is possible to shorten the length of the hollow needle 5 without mounting any O-ring at the hollow needle 5. Therefore, flexibility of the distal end of the outer sheath tube 3 can be increased even with the hollow needle 5 intervened. If the flexibility of the distal end of the outer sheath tube 3 is increased, it becomes easier to carry out insertion of the outer sheath tube 3 into the channel of the endoscope even if the insertion portion is bent when inserting the outer sheath tube 3 into the channel of the endoscope. Further, since the hollow tube 5 is hardly caught by the channel when operating to bend the distal end of the insertion portion, operation of extending the hollow needle 3 from the distal end of the outer sheath tube 3 can be facilitated.

Still further, by fitting the O-ring 8 in the groove 16, it is possible to prevent the O-ring 8 from slipping forward or backward with respect to the hollow needle 5.

Figure 9:
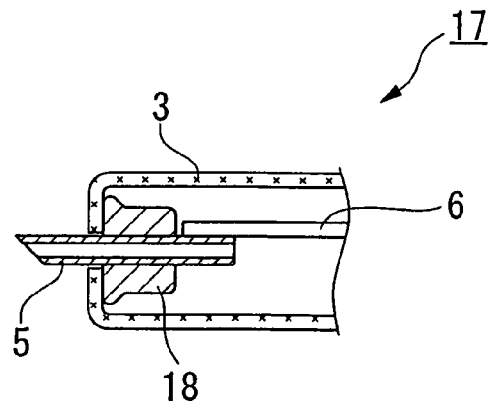
FIG. 9 is a sectional view depicting the major parts of a needle for an endoscope according to Embodiment 4 of the invention along the axial direction thereof.

Next, a description is given of Embodiment 4 of the needle for an endoscope according to the invention with reference to FIG. 9. Also, components which are similar to those of the respective embodiments described above are given the same reference numerals, and description thereof is omitted.

In a needle 17 for an endoscope according to the present embodiment, the hollow needle 5 is not provided with any O-ring. A diameter-enlarged portion 18 is composed of a resiliently deformable material. The diameter-enlarged portion 18 is resiliently deformed when being pushed to the diameter-reduced portion 2, and it is made coherent to the inside face of the diameter-reduced portion 2.

The needle 17 for an endoscope may be used in the same manner as the needle 1 for an endoscope according to Embodiment 1, and can bring about actions and effects which are similar to those thereof. Furthermore, since the diameter-enlarged portion 18 concurrently functions as a sealing member, the length of the hollow needle 5 can be shortened. Accordingly, flexibility of the distal end of the outer sheath tube 3 can be increased even with the hollow needle 5 intervened. If the flexibility of the distal end of the outer sheath tube 3 is increased, operations of inserting the outer sheath tube 3 through the channel and of extending the hollow needle 3 from the distal end of the outer sheath tube 3 can be facilitated as described in the description of Embodiment 3.

In addition, since the diameter-enlarged portion 18 concurrently functions as a sealing member, it is possible to reduce the number of components, wherein the production costs can be reduced.

Figure 10:
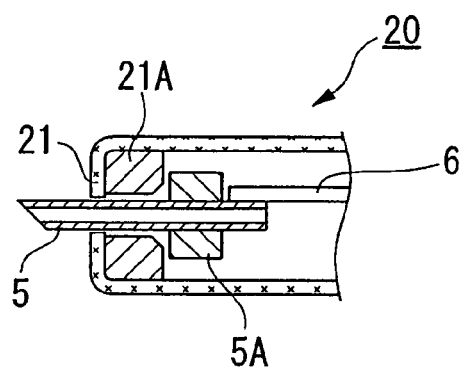
FIG. 10 is a sectional view depicting the major parts of a needle for an endoscope according to Embodiment 5 of the invention along the axial direction thereof.
Figure 11:
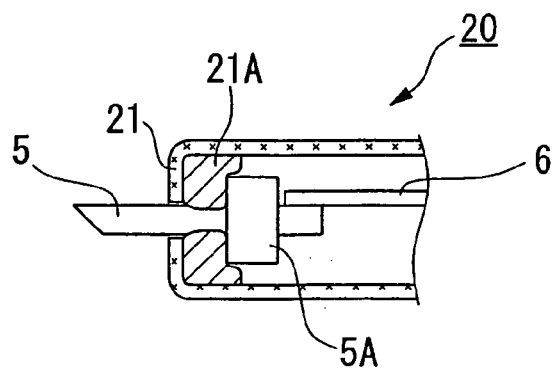
FIG. 11 is a sectional view depicting the major parts of a needle for an endoscope according to Embodiment 5 of the invention along the axial direction thereof.

Next, a description is given of Embodiment 5 of the needle for an endoscope according to the invention with reference to FIG. 10 and FIG. 11. Further, components which are similar to those of the respective embodiments described above are given the same reference numerals, and description thereof is omitted.

In a needle 20 for an endoscope according to the embodiment, the hollow needle 5 is not provided with a sealing member such as an O-ring, wherein a sealing member 21A is disposed in a diameter-reduced portion 21 as depicted in FIG. 10. The sealing member 21A is made of a resiliently deformable material and is made thick and cylindrical. The sealing member 21A is resiliently deformed when the diameter-enlarged portion 5A is pushed thereinto, and is made coherent to the front end face of the diameter-enlarged portion 5A.

According to the needle 20 for an endoscope, since the sealing member 21A is resiliently deformed and is made coherent to the diameter-enlarged portion 5A as depicted in FIG. 11 if the diameter-enlarged portion 5A is pushed into the diameter-reduced portion 21, actions and effects which are similar to those of Embodiment 4 described above can be brought about.

Also, since the sealing member 21A is fixed at a fixed position and does not move with respect to the outer sheath tube 3, there is no need to take dropping off of the sealing member from the hollow needle into consideration.

Figure 12:
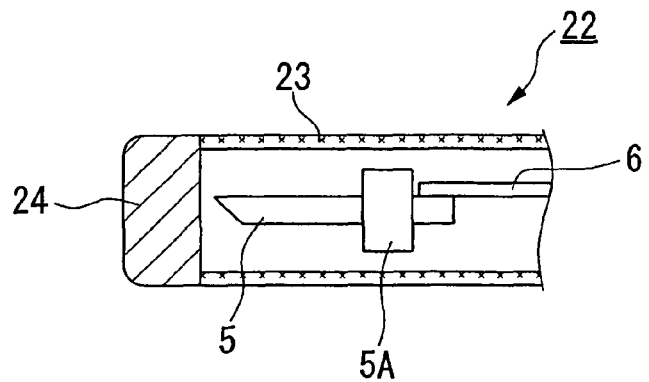
FIG. 12 is a sectional view depicting the major parts of a needle for an endoscope according to Embodiment 6 of the invention along the axial direction thereof and depicts a state where the diameter-reduced portion is separated from the diameter-enlarged portion.
Figure 13:
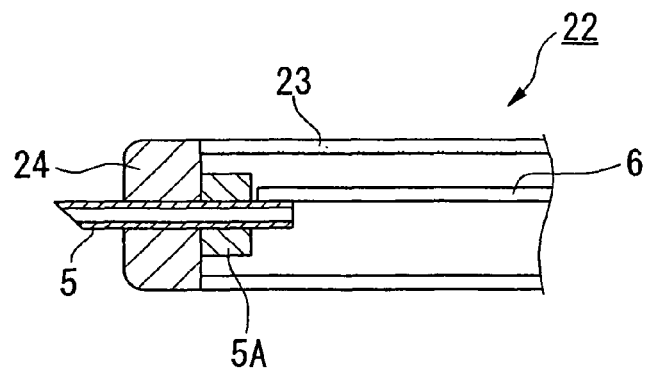
FIG. 13 is a sectional view depicting the major parts of a needle for an endoscope according to Embodiment 6 of the invention along the axial direction thereof and depicts a state where the diameter-enlarged portion is made coherent to the diameter-enlarged portion.

Next, a description is given of Embodiment 6 of the needle for an endoscope according to the invention with reference to FIG. 12 and FIG. 13. Also, components which are similar to those of the respective embodiments described above are given the same reference numerals, and description thereof is omitted.

A needle 22 for an endoscope according to the present embodiment is not provided with a diameter-reduced portion. As depicted in FIG. 12 and FIG. 13, a cover portion 24 to block the distal end of an outer sheath tube 23 is formed. The cover portion 24 is composed of an elastic material such as a synthetic resin so that the needle tip of the hollow needle 5 can be penetrated therethrough.

In the needle 22 for an endoscope, the outer sheath tube 23 is passed through the channel of the endoscope, and the hollow needle 5 is inserted into the inside face of the cover portion 24 by operating the operation portion 7, wherein the needle tip of the hollow needle 5 is extended from the outside face of the cover portion 24. Then, the hollow needle 5 extended from the cover portion 24 is inserted into a bodily tissue. Further, a drug solution is supplied into the fluid passage of the outer sheath tube 23, and the drug solution is discharged from the distal end of the hollow needle 5, wherein the drug solution is injected into a lesion. Since the distal end of the outer sheath tube 23 is blocked by the cover portion 24, and the hollow needle 5 is inserted into the cover portion 24 made of an elastic material and is extended from the distal end of the outer sheath tube 23, no drug solution leaks outside the outer sheath tube 23.

According to the needle 22 for an endoscope, since the interior of the outer sheath tube 23 is kept sealed until the hollow needle 5 is extended from the cover portion 24, it is possible to maintain a sterilized state. Also, since the cover portion 24 can be comparatively easily processed, the production cost can be reduced.

Figure 14:
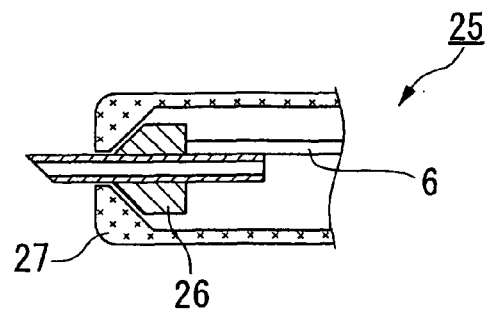
FIG. 14 is a sectional view depicting the major parts of a needle for an endoscope according to Embodiment 7 of the invention along the axial direction thereof.

Next, a description is given of Embodiment 7 of the needle for an endoscope according to the invention with reference to FIG. 14. Also, components which are similar to those of the respective embodiments described above are given the same reference numerals, and description thereof is omitted.

A needle 25 for an endoscope according to the present embodiment is not provided with a sealing member. While the outer diameter of the outer circumferential surface of a diameter-enlarged portion 26 gradually increases from the distal end of the outer sheath tube 23 toward the proximal end thereof, the inner diameter of a diameter-reduced portion 27 is gradually enlarged from the distal end of the outer sheath tube 23 toward the proximal end thereof. The inclination of the outer circumferential surface of the diameter-enlarged portion 26 is almost made coincident with the inclination of the inner circumferential surface of the diameter-reduced portion 27, wherein if the diameter-enlarged portion 26 is pushed into the diameter-reduced portion 27, the outer circumferential surface of the diameter-enlarged portion 26 is brought into contact with the inner circumferential surface of the diameter-reduced portion 27.

The needle 25 for an endoscope may be used in the same manner as the needle 1 for an endoscope according to Embodiment 1, and can bring about actions and effects which are similar to those of Embodiment 1. Further, since the outer circumferential surface of the diameter-enlarged portion 26, which is formed to be tapered, is brought into facial contact with the inner circumferential surface of the diameter-reduced portion 27, which is also formed to be tapered, a drug solution can be prevented from leaking out between the diameter-enlarged portion 26 and the diameter-reduced portion 27 when injection pressure is applied to the drug solution.

According to the needle 25 for an endoscope, since no sealing member such as an O-ring, etc., is required, it is not necessary to take dropping off thereof into consideration. Further, it is possible to reduce the production costs.

Figure 15:
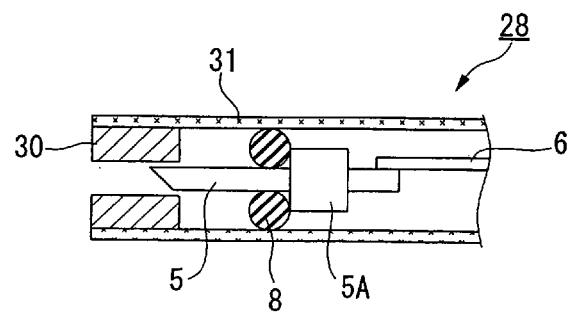
FIG. 15 is a sectional view depicting the major parts of a needle for an endoscope according to Embodiment 8 of the invention along the axial direction thereof.

Next, a description is given of Embodiment 8 of the needle for an endoscope according to the invention with reference to FIG. 15. Also, components which are similar to those of the respective embodiments described above are given the same reference numerals, and description thereof is omitted.

In a needle 28 for an endoscope according to the present embodiment, the length of a diameter-reduced portion 30 along the moving direction of the hollow needle 5 is formed to be longer than the moving distance of the hollow needle 5 when the hollow needle 5 is extended from and retracted into the distal end of an outer sheath tube 31. In addition, the diameter-reduced portion 30 is composed of an easily flexible elastic material. The needle tip of the hollow needle 5 is not completely pulled off from the diameter-reduced portion 30 even in a state where the hollow needle 5 is retracted from the distal end of the outer sheath tube 31, and the needle tip is disposed inside the diameter-reduced portion 30.

The needle 28 for an endoscope may be used in the same manner as the needle 1 for an endoscope according to Embodiment 1, and can bring about actions and effects which are similar to those thereof. Further, since the needle tip of the hollow needle 5 is disposed inside the diameter-reduced portion 30 even in a state where the hollow needle 5 is retracted from the distal end of the outer sheath tube 31, it is possible to prevent such a situation where the hollow needle 5 cannot be extended from the outer sheath tube 31 due to the needle tip being inserted into the diameter-reduced portion 30. In addition, since the needle tip of the hollow needle 5 is disposed inside the diameter-reduced portion 30, the diameter-reduced portion 30 is engaged with the O-ring 8 even if the O-ring 8 is going to drop off from the needle tip, wherein it is possible to prevent the O-ring 8 from dropping off. Further, since the engaging portion 30 is composed of an elastic material, and flexibility of the distal end of the outer sheath tube 31 can be maintained, there is no case where it becomes difficult for the outer sheath tube 31 to be inserted into the channel.

Figure 16:
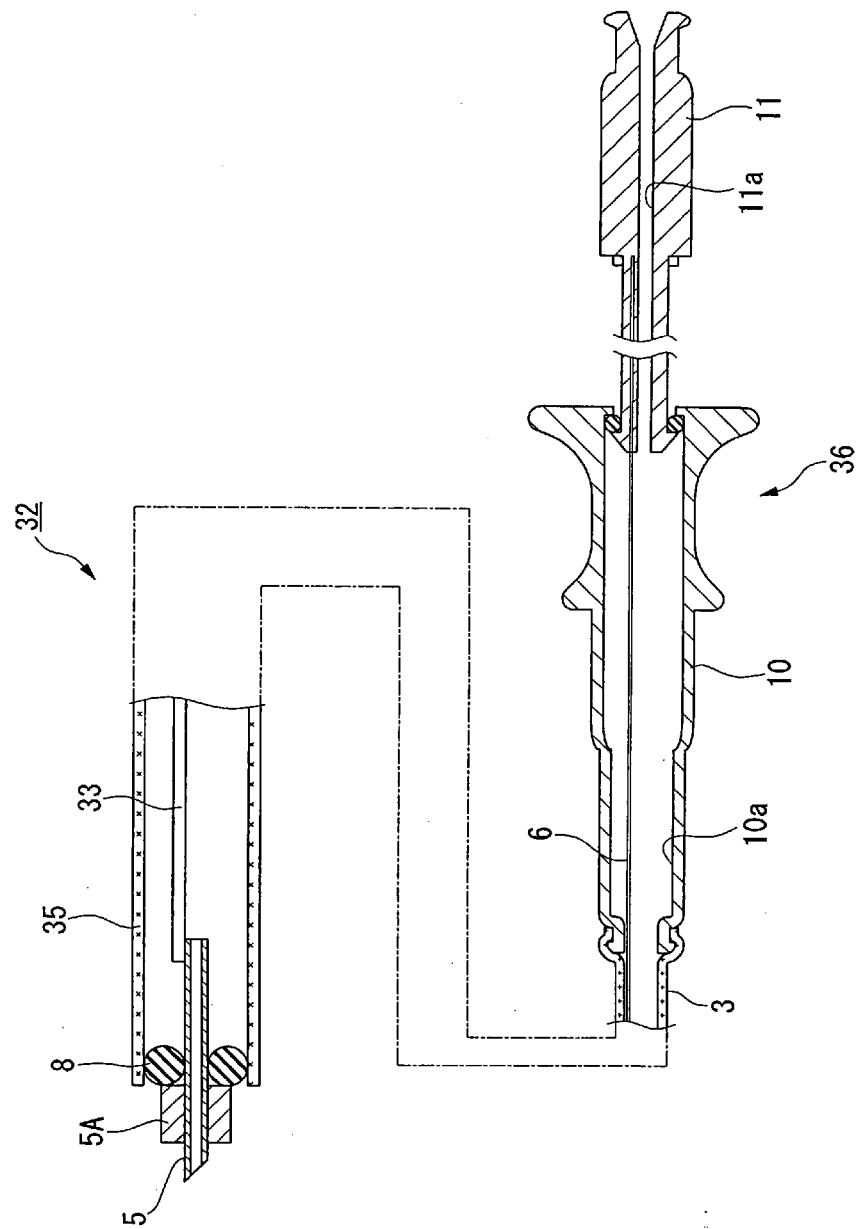
FIG. 16 is a sectional view depicting a needle for an endoscope according to Embodiment 9 of the invention along the axial direction.

Next, a description is given of Embodiment 9 of the needle for an endoscope according to the invention with reference to FIG. 16. Also, components which are similar to those of the respective embodiments described above are given the same reference numerals, and description thereof is omitted.

A needle 32 for an endoscope according to the present embodiment is not provided with a diameter-reduced portion, and the distal end of an outer sheath tube 35 is opened. A wire 33 is set to such a length at which the hollow needle 5 is held up at the position when the wire 33 is moved forward in the interior of the outer sheath tube 35 and the hollow needle 5 is extended from the distal end of the outer sheath tube 35. Also, the O-ring 8 is disposed at the rear end of the diameter-enlarged portion 5A, and is fixed at the hollow needle 5.

In the needle 32 for an endoscope, there is no need to provide a diameter-reduced portion and a cover portion at the distal end of the outer sheath tube 35, wherein, since the distal end structure of the outer sheath tube 35 is simplified, processing performance of the outer sheath tube 35 can be improved. Further, since the insertion depth of the hollow needle 5 into a bodily tissue is regulated to the length of the needle tip of the hollow needle 5, which is extended from the diameter-enlarged portion 5A, at maximum, accuracy of an operation can be improved.

Figure 17:
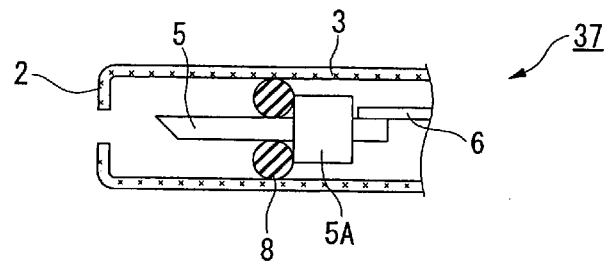
FIG. 17 is a sectional view depicting the major parts of a needle for an endoscope according to Embodiment 10 of the invention along the axial direction thereof.

Next, a description is given of Embodiment 10 of the needle for an endoscope according to the invention with reference to FIG. 17. Also, components which are similar to those of the respective embodiments described above are given the same reference numerals, and description thereof is omitted.

In a needle 37 for an endoscope according to the present embodiment, the O-ring 8 is in contact with the inside face of the outer sheath tube 3 without any clearance. Since the O-ring 8 is in contact with the inside face of the outer sheath tube 3 without any clearance, there is no case where a drug solution leaks out between the O-ring 8 and the inside face of the outer sheath tube 3 even in a state where the hollow needle 5 is retracted, that is, in a state where the O-ring 8 is not in contact with the diameter-reduced portion 2.

Figure 18:
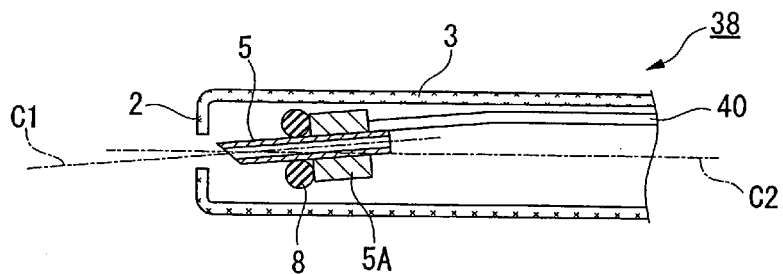
FIG. 18 is a sectional view depicting the major parts of a needle for an endoscope according to Embodiment 11 of the invention along the axial direction thereof.

Next, a description is given of Embodiment 11 of the needle for an endoscope according to the invention with reference to FIG. 18. Also, components which are similar to those of the respective embodiments described above are given the same reference numerals, and description thereof is omitted.

In a needle 38 for an endoscope according to the present embodiment, since a wire 40 to which the hollow needle 5 is connected is slightly bent and plastically deformed, the hollow needle 5 is disposed so that a center axis C1 of the hollow needle 5 diagonally crosses a center axis C2 of the diameter-reduced portion 2. The bending angle of the wire 40 is such that the wire 40 is caused to go along the inside face of the outer sheath tube 3, and the needle tip of the hollow needle 5 overlaps the center axis C2 of the diameter-reduced portion 2.

The needle 38 for an endoscope may be used in the same manner as s the needle 1 for an endoscope according to Embodiment 1, and can bring about actions and effects which are similar to those thereof. Further, since the needle tip of the hollow needle 5 overlaps the center axis C2 of the diameter-reduced portion 2 if the wire 40 is caused to go along the outer sheath tube 3, no delicate work is required in assembling. Still further, since the needle tip of the hollow needle 5 is not inserted into the inside face of the diameter-reduced portion 2 when extending the hollow needle 5 from the distal end of the outer sheath tube 3, it is possible to accurately carry out correct operations. In addition, since the wire 40 is made of a metallic material and is plastically deformed only by bending, processing of the wire 40 can be very simply carried out, wherein the production costs can be reduced.

Figure 19:
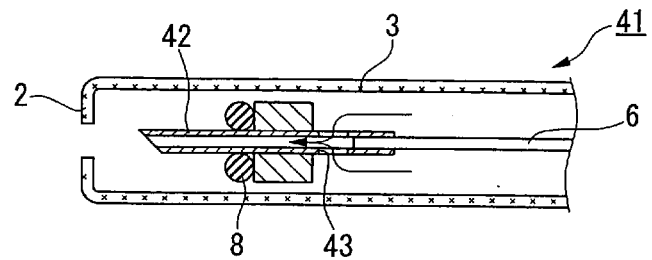
FIG. 19 is a sectional view depicting the major parts of a needle for an endoscope according to Embodiment 12 of the invention along the axial direction thereof.

Next, a description is given of Embodiment 12 of the needle for an endoscope according to the invention with reference to FIG. 19. Also, components which are similar to those of the respective embodiments described above are given the same reference numerals, and description thereof is omitted.

In a needle 41 for an endoscope according to the present embodiment, a hole portion 43 penetrating the tubular wall is formed in a hollow needle 42 at the proximal end side from the diameter-enlarged portion. The wire 40 is inserted from the proximal end of the hollow needle 42 into the tube and is connected to the hollow needle 42 by caulking, etc.

The hole portion 43 is formed so that the area of its opening is made larger than the sectional area inside the hollow needle 42. Therefore, the inside sectional area of the hollow needle 42 is the smallest in the paths through which a drug solution is conveyed.

The needle 41 for an endoscope may be used in the same manner as the needle 1 for an endoscope according to Embodiment, and can bring about actions and effects which are similar to those thereof. Furthermore, since the hollow needle 42 and the wire 6 are connected to each other with the center axes thereof made coincident with each other, the diameter of the hollow needle can be made smaller than in a case where the wire is connected to the outer circumferential surface of the hollow needle. Therefore, the outer diameter of the outer sheath tube 3 can be made further smaller, wherein it becomes easier to insert the outer sheath tube 3 into the channel and becomes easier for the hollow needle 5 to be inserted into a bodily tissue. In addition, since the inner diameter of the outer sheath tube 3 can be made small with the outer diameter thereof unchanged, the thickness of the outer sheath tube 3 can be made further thicker, wherein the outer sheath tube 3 is made tougher against buckling.

Figure 20:
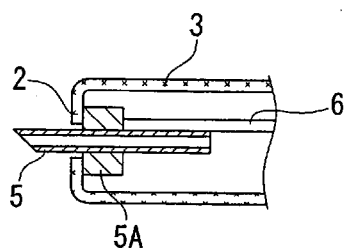
FIG. 20 is a sectional view depicting the major parts of a needle for an endoscope according to another embodiment of the invention along the axial direction thereof.

In this connection, in the respective embodiments described above, although a sealing member is provided in the hollow needle to prevent a drug solution from leakage, as depicted in FIG. 20, there is no need to provide the sealing member if the diameter-enlarged portion 5A and the engaging portion 2 are made coherent directly to each other and sufficient fluid-tightness can be secured therebetween.

Figure 21:
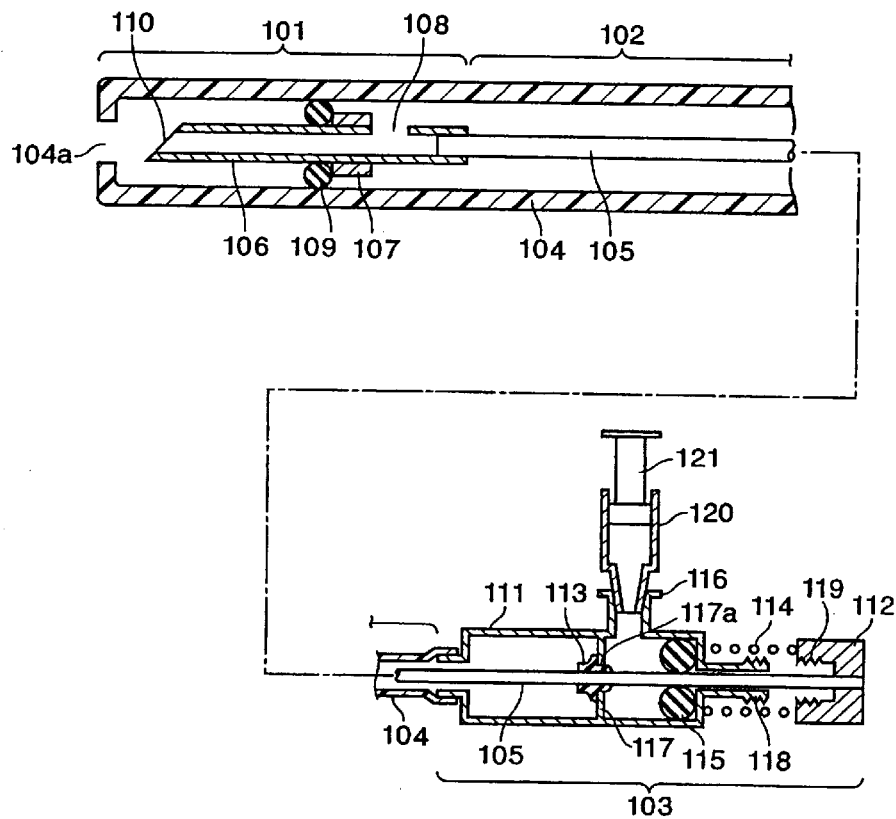
FIG. 21 is a sectional view of the entirety of one embodiment according to the invention in a state where the hollow needle thereof is accommodated in a tube with a part of the needle for an endoscope omitted.
Figure 22:
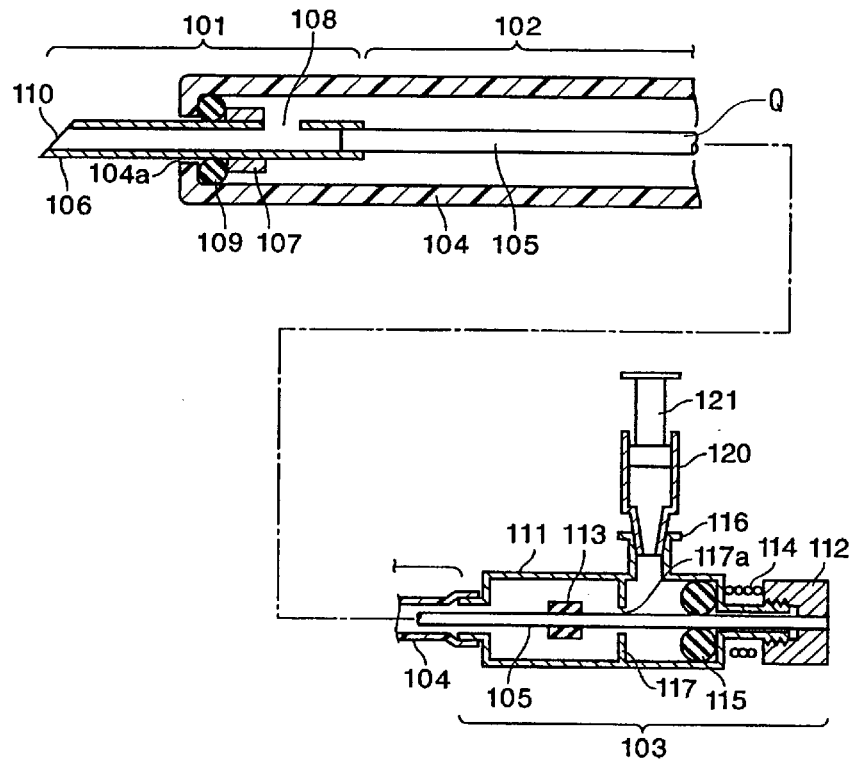
FIG. 22 is a sectional view of the entirety of the embodiment according to the invention in a state where the hollow needle thereof is extended from the tube with a part of the needle for an endoscope omitted.
Figure 23:
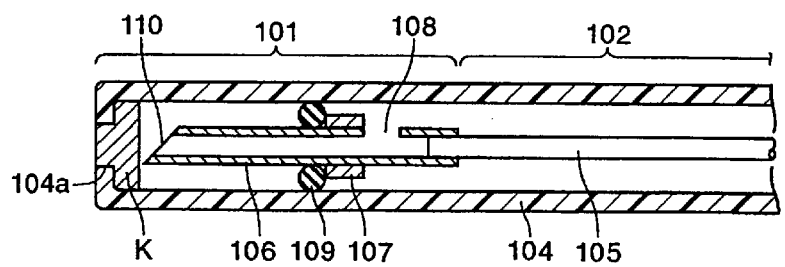
FIG. 23 is a sectional view depicting the distal end of the needle for an endoscope according to the embodiment in a state where an air layer K is provided in the distal end of the tube.

Next, a description is given of one embodiment of an instrument for an endoscope according to the invention with reference to FIG. 21 through FIG. 23.

FIG. 21 and FIG. 22 are sectional views depicting one embodiment of the invention with a part of the needle for an endoscope according to the embodiment omitted, and FIG. 23 is a sectional view depicting the distal end of a needle for an endoscope according to the same embodiment. Also, FIG. 21 is a view depicting a state where a hollow needle 106 as the distal end discharge portion is accommodated in a tube 104 as an outer sheath tube, FIG. 22 is a view depicting a state where the distal end of the hollow needle 106 is extended from the tube 104, and FIG. 23 is a view depicting a state where an air layer K is formed at the distal end of the tube.

The needle for an endoscope, which operates as an instrument for an endoscope, is composed of a distal needle portion 101, an insertion portion 102 and an operation portion 103 as operating device.

The insertion portion 102 is provided with the tube 104 made of a synthetic resin having resiliency such as, for example, fluorinated resin, polyethylene or polyamide, etc., and a wire 105 (a single strand or twisted wires) which is disposed in the tube 104 and relatively movable relative to the tube 104.

At the distal end portion of the tube 104, the distal end needle portion 101 includes a hollow needle 106 connected to the distal end of the wire 105 by welding or caulking, a pipe-shaped diameter-enlarged member 107 connected to the outer circumferential surface of the hollow needle 106 by being processed by welding or caulking, a side hole 108 opened at the circumferential surface portion from the proximal end of the diameter-enlarged member 107 at the hollow needle 106 to the vicinity of the connection between the hollow portion 106 and the wire 105, and a first fluid-tight means 109, which is fluid-tight means pressure-fitted in the outer circumferential surface of the hollow needle 106 at the distal end side of the diameter-enlarged member 107 and slidable with respect to the inner wall of the tube 104.

An opening 104a drawn, by thermoforming, to such a diameter that permits the hollow needle 106 to pass through and does not permit the diameter-enlarged member 107 to pass through is provided at the distal end of the tube 104. The wire 105 is fitted in the proximal end of the hollow needle 106 and the proximal end of the hollow needle 106 is blocked. However, since the side hole 108 is provided at the circumferential surface of the hollow needle 106, a fluid can be circulated through the side hole 108 and a distal end opening portion 110 of the hollow needle. The outer circumferential surface of the first fluid-tight member 109 is brought into contact with the inner wall of the tube 104 at all times, thereby securing fluid-tightness between the outer circumferential surface of the hollow needle 106 and the inner wall of the tube 104.

The operation portion 103 includes a ferrule member 111 fluid-tightly attached to the proximal end of the tube 104, a slider 112 as operating device passing through the inner tubular cavity of the ferrule member 111 and fixed at the proximal end of the wire 10 protruding from the proximal end of the ferrule member 111, a sealing member 113 that composes blocking device attached to the circumferential surface of the wire 105 in the ferrule member 111, a spring member 114 intervening between the ferrule member 111 and the slider 112 and resiliently pressing the slider 112 in the direction parting from the ferrule member 111, and a second fluid-tight member 115 as proximal fluid-tight means disposed on the inner surface of the proximal end of the ferrule member 111 and providing fluid-tightness between the wire 105 and the inner surface of the ferrule member 111.

The ferrule member 111 is a hollow component. The distal end portion thereof is attached to the tube 104, and the ferrule member 111 can freely circulate a fluid to the tube 104. The inner tubular cavity of the ferrule member 111 is bifurcated in the vicinity of the middle thereof, and a ferrule portion 116 is provided at the terminal part of the bifurcated tubular cavity. A syringe 120 that composes fluid supplying means is attached to the ferrule portion 116.

In addition, a receiver portion 117 including an orifice 117b, having a clearance with respect to the wire 105, whose dimensions are set so as not to permit the sealing member 113 to pass through is integrally provided at the distal end side from the bifurcated part of the inner tubular cavity of the ferrule member 111. The sealing member 113 and the orifice 117b compose the blocking device, wherein the relative relationship between the sealing member 113 and the orifice 117b is as described below.

That is, when the slider 112 is pushed out from a state depicted in FIG. 21 to the distal end side against an elastic force of the spring member 114, and the distal end of the hollow needle 106 is extended from the distal end opening portion 104a of the tube 104 as depicted in FIG. 22, the sealing member 113 is separated from the receiver portion 117, and the orifice 117b is opened. Therefore, a fluid circulation duct Q by which circulation of a fluid is made free is formed from the syringe 120 to the distal end opening 110 of the hollow needle via the inner tubular cavity of the ferrule member 111, the orifice 117b of the receiver portion 117, the interior of the tube 104, and the side hole 108 of the hollow needle 106.

In addition, when the resilient restoration force of the spring member 114 is operated onto the slider 112 from the state depicted in FIG. 22 at maximum as shown in FIG. 21, and the slider 112 is returned to the position where the slider is drawn out to the extremely proximal side, the wire 105 simultaneously moves, wherein the hollow needle 106 is completely accommodated in the tube 104. Also, the sealing member 113 is pushed into the receiver portion 117, and a part of the sealing member 113 is deformed while being collapsed due to influence of the resilient restoration force of the spring member 114, wherein the part of the sealing member 113 is forcibly inserted into the orifice 117b, and the state is maintained.

Based thereon, the sealing member 113 completely blocks the orifice 117b of the receiver portion 17 along with the wire 105, and the interior of the ferrule member 111 is divided into both side sections, using the receiver portion 117 as the boundary. When the entirety of the needle for an endoscope is observed, the fluid circulation duct Q formed between the syringe 120 and the distal end opening 10 of the hollow needle is blocked, thereby regulating circulation of a fluid.

It is preferable that a resilient material is employed for the sealing member 113 so that the sealing member 113 is reliably collapsed and deformed to completely block the orifice 117b and to reliably block a fluid. Also, at the proximal end of the ferrule member 13, a male screw 118 is provided at the ferrule member 11 and a female screw 119 is provided at the slider 112 side, so that the ferrule member 111 and the slider 112 are screwed together when being pushed in, in order to reliably retain the position of the slider 112 when the slider 112 is pushed in.

The needle for an endoscope is thus constructed, wherein the slider 112 is pushed into the ferrule member 111 side against the elastic force of the spring member 114, the slider 112 is turned in a state where it is pushed in, and the slider 112 is screwed into the ferrule member 111. Thereby, the positions of the slider 112 and the ferrule member 111 are relatively fixed, and a state where the hollow needle 106 is extended from the distal end of the tube 104 is retained.

The sealing member 113 is spaced from the receiver portion 117 and the orifice 117b is opened, wherein the fluid circulation duct Q is secured between the syringe 120 and the distal end opening 110 of the hollow needle 106, and fluid circulation is enabled. In this state, the syringe 120 in which a drug solution as a fluid is filled is attached to the ferrule portion 116, and the drug solution is sent into the tube 104 by pressing a plunger 121 provided in the syringe 120. The plunger 121 is pressed until the drug solution is discharged from the distal end of the hollow needle 106, thereby filling the interior of the tube 104 with the drug solution.

That is, the drug solution supplied from the syringe 120 is filled from the ferrule member 111 to the distal end opening 110 of the hollow needle 106 via the tube 104, the side hole 108 of the hollow needle 106 and the interior of the hollow needle 106. At this time, since the first fluid-tight means 109 and the second fluid-tight means 115 are incorporated, a fluid-tight state is secured between the hollow needle 106 and the inner wall of the tube 104 and between the inner wall of the ferrule member 111 and the wire 105, wherein the drug solution does not leak out of portions other than the distal end opening 110 of the hollow needle.

After a necessary amount of drug solution is supplied from the syringe 120 to the tube 104, the slider 112 is inversely turned to cancel engagement with the ferrule member 111. Accordingly, the resilient restoration force of the spring member 114 operates on the slider 112, and the slider 112 is returned to the proximal side. Simultaneously, the wire 105 connected to the slider 112 is drawn out from the tubular cavity in the tube 104 which is formed of the second fluid-tight means 115, wherein the redundant volume of the interior of the tube 104 is increased. To the contrary, since the redundant volume of the drug solution in the tube 104 remains unchanged, air equivalent to the increased redundant volume penetrates through the distal end of the tube 104 where it is easiest for air to enter, and an air layer K is formed at the distal end of the tube 104 as depicted in FIG. 23.

Further, as the spring member 114 is elongated to the maximum and the slider 112 is returned to the extreme proximal end side, the sealing member 113 attached to the wire 105 is pushed into the receiver portion 117 to completely block the orifice 117b. Therefore, the fluid circulation duct Q formed between the syringe 120 and the distal end opening 110 of the hollow needle is blocked. Accordingly, the end portion opposite the distal end opening 110 of the hollow needle does not become a movable end of the plunger 121, and is turned into a blocked end.

Next, a needle for an endoscope according to the invention is inserted into a channel of the endoscope, which is not shown, and the distal end of the tube 104 is extended from the distal end of the endoscope. After that, the slider 112 is pushed into the ferrule member 111, and the distal end of the hollow needle 106 is extended from the distal end of the tube 104. Also, the slider 112 is further pushed into and is screwed with the ferrule member 111. Thus, a state where the distal end of the hollow needle 106 is extended from the distal end opening 104a of the tube 104 is retained.

In addition, by pushing the slider 112 in, a part of the wire 105 positioned at the proximal end side of the second fluid-tight means 115 passes through the second fluid-tight means 115 and is pushed into the ferrule member 111 and the tubular cavity of the tube 104, which are filled with a drug solution. Accordingly, the redundant volume of the fluid tubular cavity of the ferrule member 111 and the tube 104 is reduced, air existing in the distal end of the tube 104, which forms the air layer K, is pushed out from the distal end opening 104a of the tube 104, wherein the interior of the tube 104 is completely filled with the drug solution. Simultaneously, since the sealing member 113 is spaced from the receiver portion 117 to open the orifice 117b, the fluid circulation duct Q between the syringe 120 and the distal end opening 110 of the hollow needle is secured to enable circulation of the drug solution.

After that, the hollow needle 106 protruding from the distal end of the tube 104 is inserted into a lesion, and the drug solution is injected into the lesion through the hollow needle 106 by pushing the plunger 121 in, which is provided in the syringe 120. By retracting the slider 112 after an adequate amount of the drug solution is injected, the hollow needle 106 is accommodated in the tube 104. Where inserting of the hollow needle and injection of a drug solution are required at a plurality of points, the above-described action is repeated a plurality of times. Also, by pulling out the tube 104 led from the proximal side of the endoscope, the needle for an endoscope is drawn from the endoscope. Also, where the amount of drug solution is insufficient, a new syringe 120 filled with the same drug solution may be re-attached.

As described above, in the needle for an endoscope according to the invention, the hollow needle 106 is accommodated in the tube 104, and the sealing member 113 blocks the orifice 117b provided in the receiver portion 117 of the ferrule member 111, wherein the fluid circulation duct Q formed between the syringe 120 and the distal end opening 110 of the hollow needle is blocked.

That is, since the end portion opposite the distal end opening 110 of the hollow needle is turned into a blocked end, the plunger 121 is not influenced due to the atmospheric pressure applied onto the distal end opening 104a of the tube even if the relative heights of the distal end opening 104a of the tube 104 and the plunger 121 plane of the syringe 120 change when handling the components such as inserting the hollow needle into the endoscope, wherein there is no case where the plunger 121 is pushed back or retracted.

Therefore, cumbersome work to remove air from a needle, which is carried out before inserting the needle into a lesion before, is no longer required. Further, an expensive drug solution needlessly consumed along with removal of air is no longer ejected; thus an economic advantage is brought about. Still further, there is no case where a drug solution needlessly leaks out during handling, and such a problem does not occur, by which a leaked drug solution stains a white coat and/or a floor.

In addition, work for removing a drug solution, a bodily fluid or blood from time to time in a therapy using an endoscope is carried out. In this case, since the work is carried out by a suction action via an endoscope channel, a drug solution, a bodily fluid and/or blood may remain in the endoscope channel.

Where the air layer K does not exist at the distal end of a tube as in a general injection needle, a drug solution, a bodily fluid and/or blood remaining in the endoscope channel may be brought into contact with another drug solution filled in the tube, wherein there is a risk that since these are all fluids, both of the fluids are easily mixed.

To the contrary, if the needle for an endoscope according to the invention is used, the air layer K exists at the distal end of the tube 104 in line with a retracting action of the hollow needle 106 into the tube 104. Accordingly, even if the distal end of the needle for an endoscope according to the invention is brought into contact with another drug solution, bodily fluid and/or blood remaining in the endoscope channel, these are isolated from a drug solution filled in the tube 104 by the air layer K, wherein there is no case where both are mixed together.

In addition, since the spring member 114 intervenes between the slider 112 and the ferrule member 111, a state where the sealing member 113 is reliably pushed into the receiver portion 117 can be maintained even if an external force is applied to the tube 104 when inserting the needle for an endoscope into the endoscope channel, wherein it is possible to reliably prevent air from penetrating, etc.

The invention is not limited to the above-described embodiments. It is obvious that the invention can be subjected to various modifications such as other apparatuses within a scope not departing from the spirit of the invention.

For example, in an instrument for an endoscope which feeds a fluid into a body cavity, blocking device may be provided between the proximal end feeding means and the distal end discharge port. Also, it is preferable that the instrument for an endoscope is a needle for an endoscope.

It is preferable that the needle for an endoscope for feeding a fluid into a body cavity as described above include a flexible outer sheath tube and a hollow needle, and the hollow needle is freely extended from and retracted into the outer sheath tube.

It is preferable that, in the needle for an endoscope as described above, only in a state where the hollow needle is accommodated in the outer sheath tube, fluid circulation between the proximal end feeding means and the distal end discharge port be blocked by the blocking device.

It is preferable that, in the needle for an endoscope as described above, the blocking device be carried out by a retracting action of the hollow needle into the outer sheath tube.

It is preferable that, in the needle for an endoscope as described above, fluid circulation between the proximal end feeding means and the distal end discharge port be blocked by blocking device by a resilient member attached to a wire for driving the needle being made coherent to a part of the fluid tubular cavity by a retracting action of the hollow needle into the outer sheath tube.

It is preferable that, in the needle for an endoscope as described above, an air layer be brought about at the distal end of the outer sheath tube in a state where the hollow needle is accommodated in the outer sheath tube.

It is preferable that the needle for an endoscope as described above include an outer sheath, a hollow needle having a side hole, a wire attached to the proximal end of the hollow needle for driving the hollow needle so as to be freely extended from and retracted into the outer sheath tube, and a ferrule member attached to the proximal end of the outer sheath tube, and further include distal end fluid-tight means for keeping the outer circumferential surface of the hollow needle and the inner surface of the outer sheath fluid-tight at the distal end side from the side hole of the hollow needle and proximal end fluid-tight means for keeping the inner surface of the ferrule member and the wire fluid-tight, wherein the redundant volume of space in the interior of the outer sheath is increased by pulling the wire to the proximal end with respect to the proximal end fluid-tight means.

It is preferable that, in the needle for an endoscope as described above, an action for pulling the wire to the proximal end be an action for retracting the hollow needle into the outer sheath.

It is preferable that, in the needle for an endoscope as described above, the blocking device include an orifice provided in the flexible sheath or in the operation portion body and a sealing member that is fixed at the operating wire, disposed at the distal end side from the orifice and engageable with the orifice.

The invention relates to a needle for an endoscope including: an outer sheath tube having a fluid passage formed therein; a hollow needle accommodated in the outer sheath tube so as to be extended therefrom and retracted thereinto for discharging a fluid supplied through the fluid passage; and operating device operated at the proximal end of the outer sheath tube for protruding the hollow needle from the outer sheath tube and retracting the same thereinto; wherein a diameter-reduced portion is formed at the distal end of the outer sheath tube, and a diameter-enlarged portion is formed at the hollow needle, which, when the hollow needle is extended from the distal end of the outer sheath tube, is brought into contact with the diameter-reduced portion and blocks the distal end of the outer sheath tube.

With the needle for an endoscope according to the invention, by adequately forming the thickness of the tube and adequately shaping the outer diameter, it is possible to easily carry out operations of extruding a drug solution, inserting the tube through the channel of an endoscope, and pushing the needle out of the distal end of the tube. In addition, since no expensive adhesion technique is required as in the prior arts, it is possible to reduce the production costs.

The invention relates to an instrument for an endoscope including: an outer sheath tube having a fluid passage provided therein; a distal end discharging portion that is accommodated in the distal end of the outer sheath tube so as to be extended therefrom and retracted thereinto, and is connected to the distal end of the fluid passage; operating device provided at the proximal end of the outer sheath tube for operating the distal end discharging portion so as to be extended from the distal end of the outer sheath tube and retracted thereinto; fluid supplying device, which is provided in the outer sheath tube and is caused to communicate with the fluid passage, and supplies a fluid to the distal end discharging portion through the fluid passage; and blocking device, which is provided in the fluid passage, for freely opening and shutting off circulation of a fluid in line with an operation of the operating device.

With the instrument for an endoscope according to the invention, since air is prevented from penetrating through the needle tip of the tube, a fluid is prevented from leaking from the outer sheath tube, no removal of penetrated air is required, and ease of use can be improved. Further, since a fluid is not needlessly consumed due to leakage, economic burden can be relieved. In addition, there is no case where leaked fluids stain white coats and a floor.

What is claimed is:

1. A needle for an endoscope, comprising:
   an outer sheath tube having a cylindrical shape, an inside of the outer sheath tube being a fluid passage;
   a hollow needle for discharging a fluid supplied through the fluid passage, the hollow needle being housed in the fluid passage; and
   an operating device that is operated at a proximal end of the outer sheath tube, for extending the hollow needle from a distal end of the fluid passage and retracting the hollow needle into the fluid passage; wherein
   the outer sheath tube comprising a diameter-reduced portion being formed at the distal end of the outer sheath tube;
   a hole is formed at the diameter-reduced portion so as to directly communicate with the flow passage;
   the hollow needle comprising a sealing member being brought into close contact with the diameter-reduced portion when the hollow needle extends from the distal end of the outer sheath tube;
   the hollow needle is provided so as to be capable of advancing and retracting in the fluid passage and so as to be allowed to protrude and retract a needle tip of the hollow needle from the hole such that a proximal end of the hollow needle remains within the outer sheath tube;
   the proximal end of the hollow needle directly communicates with the fluid passage within the outer sheath tube; and
   when the fluid is supplied to the fluid passage in a state where the needle tip of the hollow needle protrudes from the hole, the fluid flows into the hollow needle through the proximal end of the hollow needle, and then is discharged from the needle tip.

2. The needle for an endoscope according to claim 1, further comprising a diameter-enlarged portion which is formed at the hollow needle, wherein
   the sealing member is provided at the front end of the diameter-enlarged portion.

3. The needle for an endoscope according to claim 2, wherein the sealing member is brought into contact with the diameter-reduced portion and is resiliently deformed to be made coherent to the diameter-reduced portion.

4. The needle for an endoscope according to claim 3, wherein the sealing member is brought into contact with the diameter-reduced portion and is resiliently deformed by extending the hollow needle from the distal end of the outer sheath tube.

* * * * *